United States Patent
Falk et al.

(10) Patent No.: US 7,860,580 B2
(45) Date of Patent: Dec. 28, 2010

(54) ACTIVE FIXATION MEDICAL ELECTRICAL LEAD

(75) Inventors: Jeffrey G. Falk, Blaine, MN (US); Douglas N. Hess, Maple Grove, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 555 days.

(21) Appl. No.: 11/379,849

(22) Filed: Apr. 24, 2006

(65) Prior Publication Data

US 2007/0250144 A1 Oct. 25, 2007

(51) Int. Cl.
*A61N 1/362* (2006.01)

(52) U.S. Cl. .................. 607/127; 607/119; 607/131

(58) Field of Classification Search .............. 607/120, 607/127
See application file for complete search history.

(56) References Cited

U.S. PATENT DOCUMENTS

| | | | |
|---|---|---|---|
| 4,233,992 A * | 11/1980 | Bisping | 607/127 |
| 5,443,492 A | 8/1995 | Stokes et al. | |
| 5,551,427 A * | 9/1996 | Altman | 600/374 |
| 5,571,162 A | 11/1996 | Lin | |
| 5,755,764 A | 5/1998 | Schroeppel | |
| 5,873,866 A * | 2/1999 | Kondo et al. | 604/526 |
| 6,144,882 A | 11/2000 | Sommer et al. | |
| 6,192,280 B1 | 2/2001 | Sommer et al. | |
| 6,493,591 B1 | 12/2002 | Stokes | |
| 6,556,874 B2 | 4/2003 | Audoglio | |
| 6,931,286 B2 * | 8/2005 | Sigg et al. | 607/120 |
| 2004/0064158 A1 | 4/2004 | Klein et al. | |
| 2004/0064172 A1 * | 4/2004 | McVenes et al. | 607/122 |

* cited by examiner

*Primary Examiner*—Carl H Layno
*Assistant Examiner*—Natasha N Patel
(74) *Attorney, Agent, or Firm*—Carol F. Barry

(57) ABSTRACT

A medical electrical lead includes a proximal insulation segment, a distal insulation segment, a conductor extending within the proximal and distal segments, and an electrode coupled to the conductor and disposed in proximity to a distal end of the distal insulation segment. A fixation element of the lead is coupled to a distal end of the proximal insulation segment and includes a wire wound in a helix, which extends distally from the proximal segment, over the distal insulation segment.

37 Claims, 9 Drawing Sheets

ACTIVE FIXATION MEDICAL ELECTRICAL LEAD

TECHNICAL FIELD

The present invention pertains to medical electrical leads and more particularly to implantable medical electrical leads including active fixation elements.

BACKGROUND

Implantable medical devices, for example cardiac pacemakers and defibrillators, often include elongate medical electrical leads having one or more electrodes to sense electrical activity and deliver therapeutic stimulation. In recent years, with the advent of left ventricular pacing to alleviate heart failure, leads have been advanced into the coronary veins in order to position the electrodes of the leads at left ventricular pacing sites, typically located in proximity to the base of the left ventricle. Although a variety of left ventricular pacing leads, along with methods for implanting such leads, have been developed, there is still a need for a lead including features that facilitate delivery to, and fixation at, sites in the coronary vasculature.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
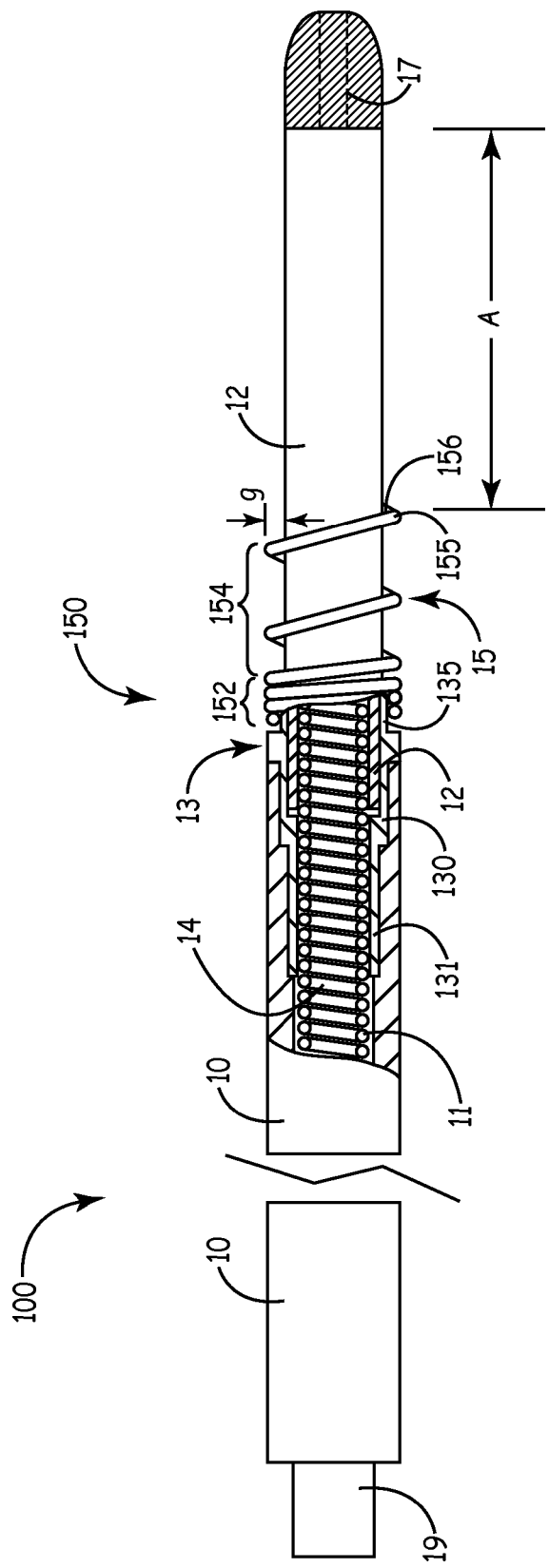
FIG. 1 is a plan view, including a partial section, of an exemplary medical electrical lead, according to some embodiments of the present invention.

FIG. 1 is a plan view, including a partial section, of an exemplary medical electrical lead 100, according to some embodiments of the present invention. FIG. 1 illustrates lead 100 including a proximal connector pin 19, a distal tip electrode 17, and an elongate conductor 11, for example, a multi-filar coil formed from MP35N alloy, which couples connector pin 19 to electrode 17. Connector pin 19 may be plugged into a port of an implantable medical device, for example a pacemaker, for electrical coupling, so that the device may send and receive electrical signals via conductor 11 and electrode 17; such a connection is well known to those skilled in the art. According to the illustrated embodiment, conductor 11 extends within a proximal insulation segment 10 and a distal insulation segment 12; proximal segment 10 generally defines a proximal portion of lead 100 and extends distally from connector pin 19; and, distal insulation segment 12 generally defines a distal portion of lead 100 and extends distally from a point in proximity to a distal end of proximal insulation segment 10 to electrode 17. Although conductor 11 is illustrated in the form of a coil, it should be noted that alternate forms of conductors, for example, cables, may be implemented within alternate embodiments of the present invention. The filars of coil 11 may each include an insulative coating, for example, Si polyimide, to electrically isolate each filar from the other so coil 11 has the capacity to provide independent circuits for more than one electrode, for example as described below.

FIG. 1 further illustrates a fixation element 150 coupled to the distal end of proximal insulation segment 10 and including a wire, which may have a diameter of approximately 0.008 inch, wound in a helix 15, which includes a tight-wound portion 152 and a space-wound portion 154; helix 15 extends distally over distal insulation segment 12 and terminates in a distal end 155, which includes a piercing tip 156. According to the illustrated embodiment, fixation element 150 further includes a stud component 13 having a distal surface 135 on which tight wound portion 152 of helix 15 is mounted for coupling, for example, via crimping or welding, and first and second proximal surfaces 130 and 131, respectively, over which proximal insulation segment 10 extends. Proximal insulation segment 10 may be adhesively bonded to one or both of proximal surfaces 130, 131. According to some embodiments of the present invention, component 13 is made of a conductive material and helix 15 functions as a second electrode of lead 100, for example, being formed of a platinum iridium alloy, and being coupled to one or more filars of multi-filar conductor coil 11; the one or more filars may be terminated in proximity to component 13 and lifted away from the other filars to engage second proximal surface 131 of component 13 for electrical coupling thereto, according to methods known to those skilled in the art, for example, via crimping or welding. Helix 15, serving as an electrode, may be of the same polarity as, or opposite polarity to, electrode 17.

Figure 2A:
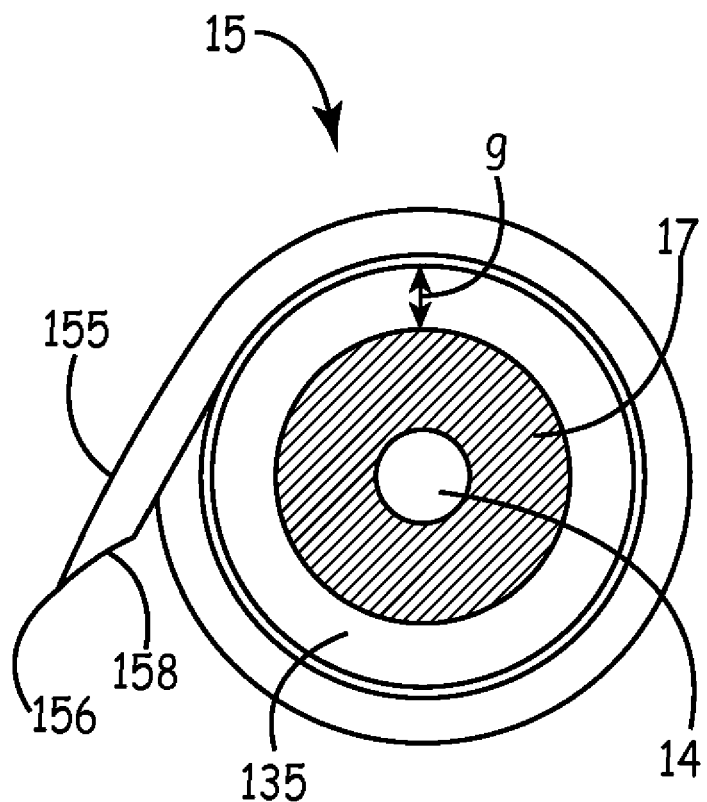
FIG. 2A is an end view of the lead shown in FIG. 1, according to one embodiment.
Figure 2B:
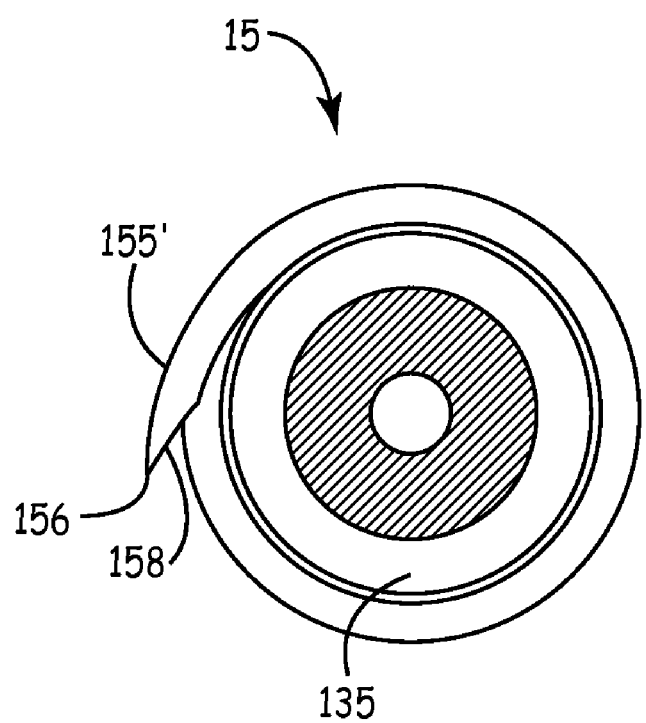
FIG. 2B is an end view of the lead shown in FIG. 1, according to an alternate embodiment.

FIG. 2A is an end view of lead 100, wherein piercing distal tip 156, according to one embodiment, is seen more clearly. FIG. 2A illustrates distal end 155 of helix 15 including a relatively flat surface 158, which may have been formed by grinding distal end 155, tapering from an inner side to an outer side of distal end 155 to form tip 156. FIG. 2A further illustrates helix distal end 155 offset, or angled outward, away from a centerline of helix 15, extending approximately tangent to a circle defined by helix 15. FIG. 2B is an end view of lead 100, according to an alternate embodiment, wherein a distal end 155' of helix 15, instead of extending tangent to a circle defined by helix 15, extends away from the circle in an eccentric path.

Figure 3A:
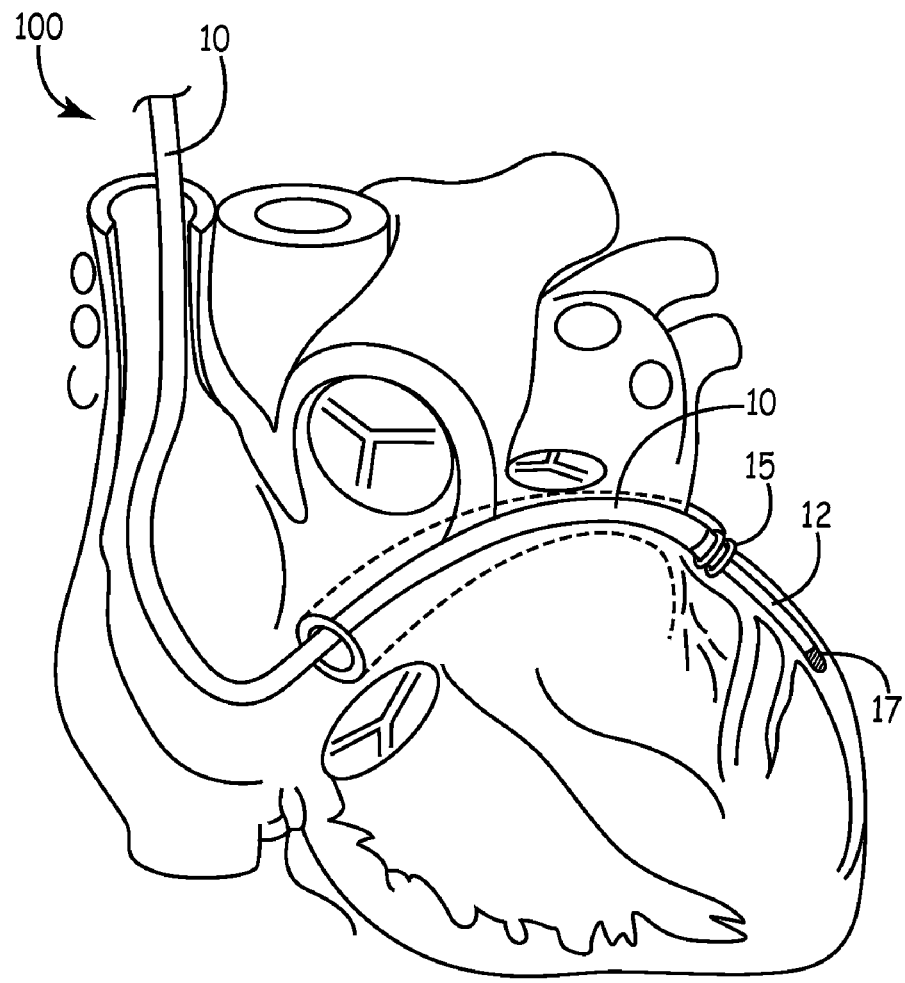
FIG. 3A is a schematic of an implanted lead, according to some embodiments of the present invention.

According to embodiments of the present invention, lead 100 may be implanted by fixing within a coronary vein, for example, to provide left ventricular pacing via electrode 17, by applying a rotational force to lead 100, in proximity to connector pin 19, which turns helix 15 so that piercing tip 156 engages and rotates through a wall of the coronary vein. FIG. 3A is a schematic of lead 100 implanted as such. Referring back to FIGS. 1 and 2, it may be seen that an outer diameter of distal insulation segment 12 relative to an inner diameter of helix 15 provides a gap g therebetween, which may be greater than or approximately equal to 0.003 inch. The inventors have found that a gap of approximately 0.003 inch is sufficient to enable engagement while still providing secure engagement; larger gaps, although viable and within the scope of the present invention, may not provide as secure engagement within a vein.

According to preferred embodiments of the present invention, proximal insulation segment 10, being between approximately 35 cm long and approximately 105 cm long, is formed of a relatively flexible material having enough torsional rigidity to transfer a torque, for example, between approximately 0.06 and approximately 0.1 in. oz., applied near pin 19 to helix 15. According to an exemplary embodiment, proximal insulation segment 10 has a wall thickness between approximately 0.005 inch and approximately 0.009 inch and is formed of a polyurethane having a durometer around 55D. According to another aspect of the preferred embodiments, distal insulation segment 12 is formed of a highly flexible material having a rigidity that is less than that of the material forming proximal insulation segment 10. Suitable materials for distal segment 12 include, but are not limited to, softer polyurethanes, i.e. around 80A durometer, and silicone rubbers. According to alternate embodiments, distal insulation segment 12 is formed of the same material as proximal insulation segment and, simply by having a smaller cross-sectional area than proximal segment 10, is less rigid than proximal segment 10. With reference to FIG. 3A, it may be appreciated that a smaller diameter and greater flexibility of distal segment 12, compared with proximal segment 10, may allow positioning of electrode tip 17 within a smaller and more tortuous coronary vein.

Figure 3B:
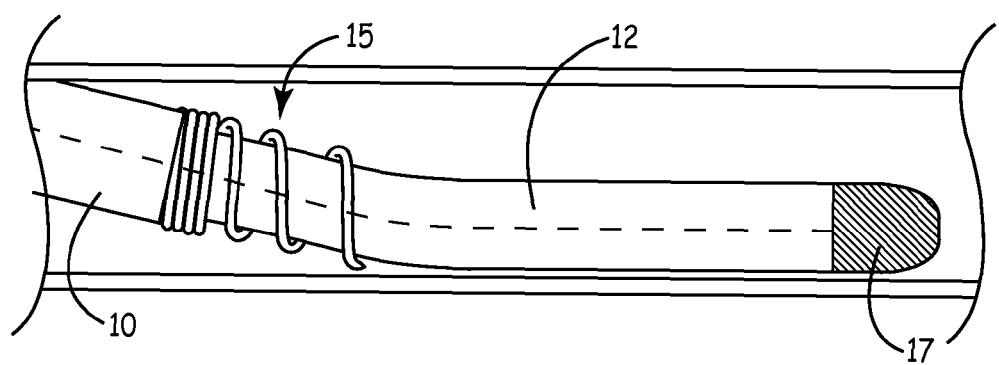
FIG. 3B is a schematic of a lead directed for fixation, according to some embodiments of the present invention.

With reference to FIGS. 1, 2 and 3A, it may be appreciated that lead 100 may be delivered to an implant site, as depicted in FIG. 3, with assistance from a stylet or guide wire inserted within a lumen 14 formed by coil conductor 11, according to methods well known to those skilled in the art. According to the illustrated embodiment, lumen 14 extends distally through electrode tip 17, thereby facilitating passage of a guide wire, which may be advanced ahead of tip 17. The portion of lumen 14 extending within tip electrode 17 may include a seal which allows passage of a guide wire but prevents ingress of bodily fluids into lumen 14; an example of a suitable seal is described in commonly assigned U.S. Pat. No. 6,192,280, salient portions of which are hereby incorporated by reference. Engaging a curved distal portion of a stylet within lumen 14, in proximity to fixation element 150, may further facilitate engagement of helix tip 156 with a vessel wall, by deflecting the distal portion of lead 100 away from tip 156, for example, as illustrated in FIG. 3B, wherein the dashed line represents the stylet.

Referring now to FIG. 1, in conjunction with FIG. 3A, it should be noted that a distance A between helix distal end or tip 156 and electrode 17 should be sufficient at least to allow bending of the distal portion of lead 100 into branch vessels of the venous anatomy; distance A is at least one centimeter, but, preferably distance A is between approximately 2 cm and approximately 3.5 cm so that helix 15 may be fixed in a more proximal larger vein while still allowing electrode 17 to be positioned deep enough within a tributary branching off that larger vein. Furthermore, an outer diameter of helix 15, as defined by tight wound portion 152 and space wound portion 154, is shown to be approximately equal to an outer diameter of proximal insulation segment 10, which may further facilitate smooth advancement of lead 100 within the coronary anatomy and/or a guiding catheter, which may also be used to implant lead 100.

Figure 4:
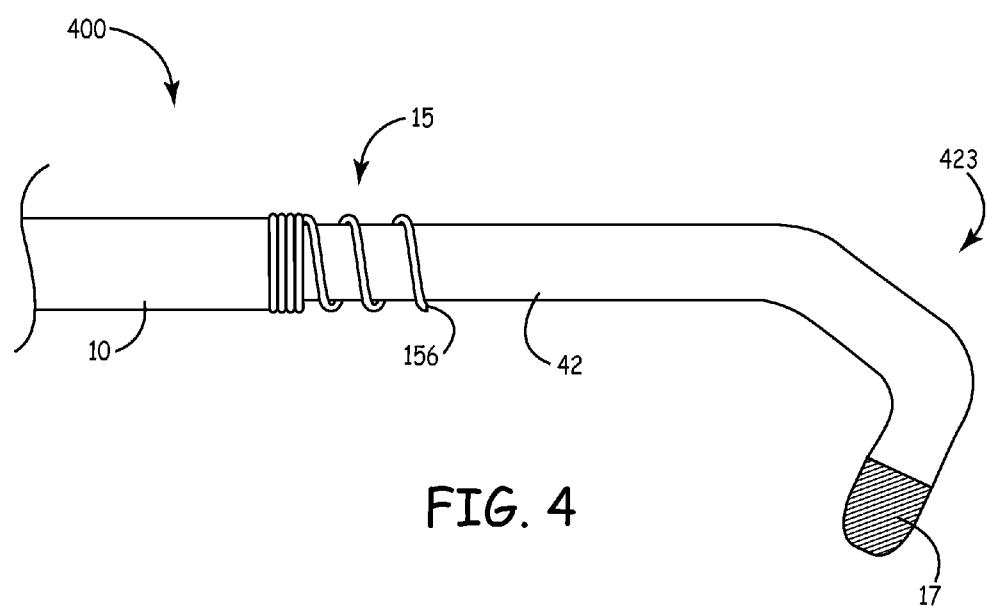
FIG. 4 is a plan view of an exemplary medical electrical lead, according to an alternate embodiment of the present invention.

FIG. 4 is a plan view of an exemplary medical electrical lead 400, according to an alternate embodiment of the present invention. FIG. 4 illustrates lead 400 including a distal insulation segment 42, generally defining a distal portion of lead 400, having a pre-formed curve 423 formed therein, according to methods known to those skilled in the art, for example, via molding or secondary heat forming; lead 400 is similar to lead 100 in other respects, for example, including proximal insulation segment 10, helix 15 and electrode tip 17. Preformed curve 423 may facilitate steering of lead 400 to a target site in the coronary vasculature and/or improve contact of electrode 17 with myocardial tissue.

Figure 5:
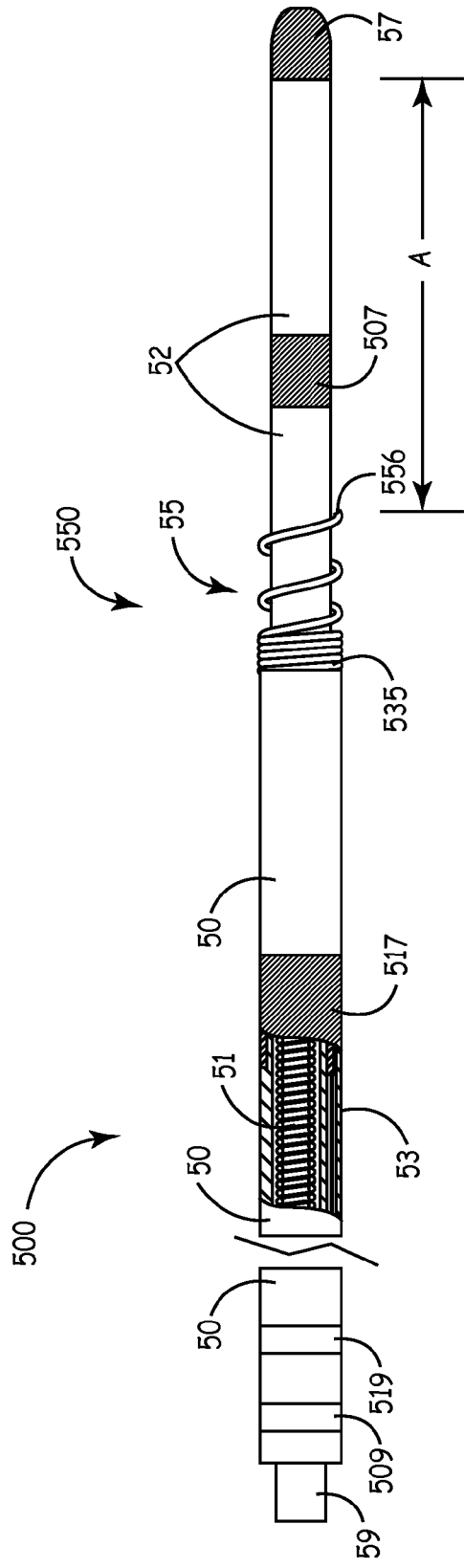
FIG. 5 is a plan view, including a partial section, of an exemplary medical electrical lead, according to additional embodiments of the present invention.

FIG. 5 is a plan view, including a partial section, of an exemplary medical electrical lead 500, according to additional embodiments of the present invention. FIG. 5 illustrates lead 500 including a first conductor 51, for example, a multi-filar coil, and a second conductor 53, for example, a cable, isolated from one another and extending side-by-side within respective lumens of a proximal insulation segment 50, which generally defines a proximal portion of lead 500; first conductor 51 further extends into a distal insulation segment 52, which generally defines a distal portion of lead 500. According to the illustrated embodiment, conductor 51 electrically couples a first electrode 57 to a connector pin 59 and a second electrode 507 to a first connector ring 509; and conductor 53 couples a third electrode 517 to a second connector ring 519. Connector pin 59 and rings 509, 519 are part of a connector that terminates a proximal end of lead 500 and may be coupled to an implantable device such that each of electrodes 507 and 57 function to pace and/or sense and electrode 517 to sense or defibrillate, according to any system configuration known to those skilled in the art.

Figure 6:
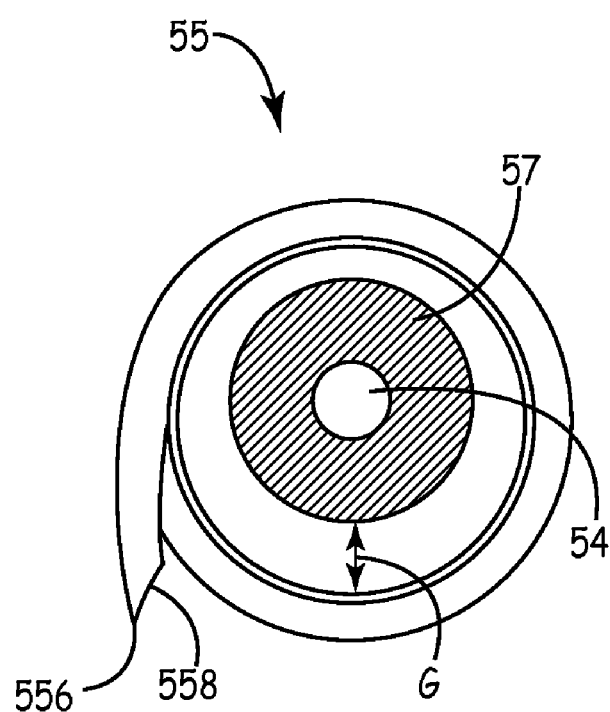
FIG. 6 is an end view of the lead shown in FIG. 5.

FIG. 5 further illustrates a fixation element 550 including a wire forming a helix 55, which is coupled to a distal end of proximal insulation element 50 and extends distally over distal insulation segment 52; element 550 may be coupled to the distal end in a manner similar to that described for fixation element 150 of lead 100. Helix 55 is shown including a piercing distal tip 556, which is spaced proximally from electrode 57 distance A as previously described for lead 100, and, similar to tip 156 of helix 15, for example, as illustrated in FIG. 6, including a relatively flat surface 558 tapering from an inner side to an outer side of helix 55. FIG. 6 is an end view of the lead shown in FIG. 5. It may be appreciated with reference to FIGS. 5 and 6 that lead 500 includes a lumen 54 extending within coil 51 and out through tip electrode 57. According to the illustrated embodiment, to accommodate conductor 53 alongside conductor coil 51, lumen 54 is offset such that distal insulation segment 52 is offset from a centerline of helix 55. Such an offset creates a gap G between helix 55 and distal segment 52, which is larger than a gap which would be created with a concentric distal segment, for example gap g shown in FIG. 2A; this larger gap G may further facilitate the engagement of helix tip 556 with a vessel wall as previously described.

Figure 7:
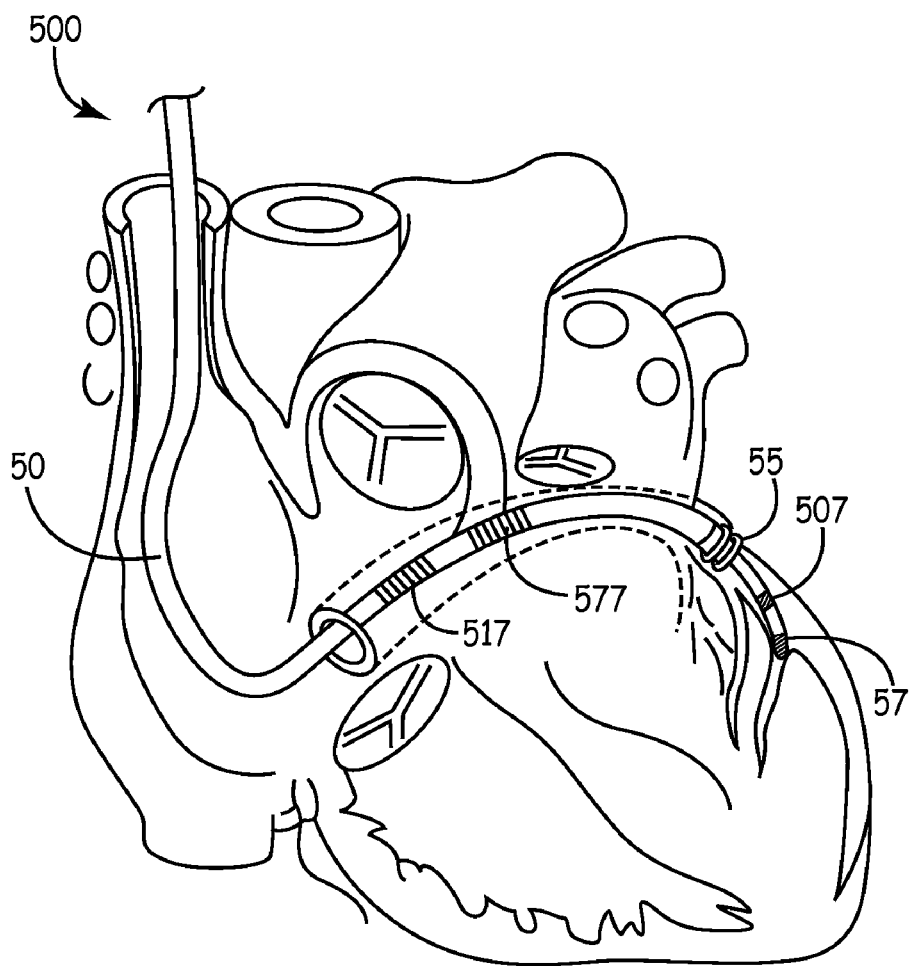
FIG. 7 is a schematic of an implanted lead, according to some embodiments of the present invention.

Lead 500 may further include a fourth electrode 577, as illustrated in FIG. 7, which is disposed proximal to helix 55 and distal to third electrode 517. FIG. 7 is a schematic showing lead 500 implanted such that electrodes 517 and 577 are disposed in the coronary sinus to sense atrial activity, and electrodes 507 and 57 are disposed in a tributary of the great cardiac vein to pace and sense the left ventricle. It should be noted that electrode 517 may further serve as a defibrillation electrode.

In the foregoing detailed description, the invention has been described with reference to specific embodiments. However, it may be appreciated that various modifications and changes can be made without departing from the scope of the invention as set forth in the appended claims.

The invention claimed is:

1. A medical electrical lead, comprising:
a distal insulation segment including a distal end;
a proximal insulation segment including a distal end disposed proximal to the distal insulation segment distal end;
an insulated conductor extending within the proximal and distal insulation segments;
an electrode coupled to the conductor and disposed in proximity to the distal insulation segment distal end; and
a fixation element coupled to the distal end of the proximal insulation segment, the fixation element including a wire wound in a helix, the helix extending distally from the proximal insulation segment, over the distal insulation segment, and the wire including a distal end terminating the helix;
the wire distal end disposed proximal to the distal insulation segment distal end, and the wire distal end including a piercing tip and a relatively flat surface tapering from an inner side of the helix to an outer side of the helix to form the piercing tip.

2. The lead of claim 1, wherein the helix wire distal end is angled outward, away from a centerline of the helix.

3. The lead of claim 1, wherein the helix wire distal end extends around an eccentric path.

4. The lead of claim 1, further comprising:
a second insulated conductor; and
a second electrode coupled to the second conductor and disposed between the helix wire distal end and the distal insulation segment distal end.

5. The lead of claim 1, further comprising:
a second insulated conductor; and
a second electrode coupled to the second conductor and disposed proximal to the fixation element.

6. The lead of claim 1, wherein the helix wire distal end is disposed proximal to the electrode at a distance greater than approximately one centimeter.

7. The lead of claim 1, wherein the distal insulation segment includes a pre-formed bend.

8. The lead of claim 1, wherein the proximal insulation segment extends over a length from a proximal end of the lead to the proximal insulation segment distal end and is formed of a material having a rigidity greater than that of a material forming the distal insulation segment.

9. The lead of claim 1, wherein the distal end of the helix angles outward and extends approximately tangent to a circle defined by a proximal portion of the helix.

10. The lead of claim 1, wherein a proximal portion of the helix defines a circle, and wherein the distal end of the helix extends away from the circle in an eccentric path.

11. The lead of claim 1, wherein the fixation element helix extends over a portion of the distal insulation segment, and wherein the entire portion of the distal insulation segment over which the fixation element helix extends is offset from a centerline of the helix.

12. The lead of claim 1, wherein distal insulation segment is offset from a centerline of the fixation element helix such that each coil of the fixation element helix is offset from the distal insulation segment by distance that is greater on one side of the distal insulation segment than on an opposite side of the distal insulation segment.

13. The lead of claim 1, the fixation element helix extends over a portion of the distal insulation segment, and wherein the entire portion of the distal insulation segment over which the fixation element helix extends is straight.

14. The lead of claim 1, wherein the distal insulation segment comprises a preformed bend located distally of the piercing tip of the helix of fixation element.

15. The lead of claim 1, wherein the flat surface comprises a ground surface formed by grinding the distal end of the fixation element.

16. The lead of claim 1, wherein the flat surface is located on an inside surface of the wire forming the helix.

17. A medical electrical lead, comprising:
a distal insulation segment including an outer diameter and a distal end;
a proximal insulation segment including a distal end disposed proximal to the distal insulation segment distal end, the proximal insulation segment extending from a proximal end of the lead to the proximal insulation segment distal end and being fowled of a material having a rigidity greater than that of a material forming the distal insulation segment;
an insulated conductor extending within the proximal and distal insulation segments;
an electrode coupled to the conductor and disposed in proximity to the distal insulation segment distal end; and
a fixation element coupled to the distal end of the proximal insulation segment, the fixation element including a wire wound in a helix, the helix extending distally from the proximal insulation segment, over the distal insulation segment, and having an inner diameter greater than the outer diameter of the distal insulation segment, wherein the helix wire includes a distal end terminating the helix, the wire distal end angled outward away from a centerline of the helix.

18. The lead of claim 17, wherein a minimum gap between the inner diameter of the helix and the outer diameter of the distal insulation segment is approximately 0.003 inch.

19. The lead of claim 17, wherein the helix wire includes a distal end terminating the helix, and further comprising:
a second insulated conductor; and
a second electrode coupled to the second conductor and disposed between the helix wire distal end and the distal insulation segment distal end.

20. The lead of claim 17, further comprising:
a second insulated conductor; and
a second electrode coupled to the second conductor and disposed proximal to the fixation element.

21. The lead of claim 17, wherein the material forming the proximal insulation segment has a durometer of approximately 55D and the material forming the distal insulation segment has a durometer of approximately 80A.

22. The lead of claim 17, wherein the wire distal end angled outward away from the centerline of the helix extends approximately tangent to a circle defined by a proximal portion of the helix.

23. The lead of claim 17, wherein a proximal portion of the helix defines a circle, and wherein the wire distal end angled outward away from the centerline of the helix extends away from the circle in an eccentric path.

24. The lead of claim 17, wherein the fixation element helix extends over a portion of the distal insulation segment, and wherein the entire portion of the distal insulation segment over which the fixation element helix extends is offset from a centerline of the helix.

25. The lead of claim 17, wherein distal insulation segment is offset from a centerline of the fixation element helix such that each coil of the fixation element helix is offset from the distal insulation segment by distance that is greater on one side of the distal insulation segment than on an opposite side of the distal insulation segment.

26. The lead of claim 17, the fixation element helix extends over a portion of the distal insulation segment, and wherein the entire portion of the distal insulation segment over which the fixation element helix extends is straight.

27. The lead of claim 17, wherein the distal insulation segment comprises a preformed bend located distally of the piercing tip of the helix of fixation element.

28. A medical electrical lead, comprising:
a distal insulation segment including a distal end;
a proximal insulation segment including a distal end disposed proximal to the distal insulation segment distal end;
an insulated conductor extending within the proximal and distal insulation segments;
an electrode coupled to the conductor and disposed in proximity to the distal insulation segment distal end; and
a fixation element coupled to the distal end of the proximal insulation segment, the fixation element including a wire wound in a helix, the helix extending distally from the proximal insulation segment, over the distal insulation segment;
the wire including a distal end terminating the helix, wherein the distal insulation segment comprises a preformed bend located distally of the distal end of the helix.

29. The lead of claim 28, further comprising:
a second insulated conductor; and
a second electrode coupled to the second conductor and disposed between the helix wire distal end and the distal insulation segment distal end.

30. The lead of claim 28, further comprising:
a second insulated conductor; and
a second electrode coupled to the second conductor and disposed proximal to the fixation element.

31. The lead of claim 28, wherein the helix wire distal end is angled outward, away from a centerline of the helix.

32. The lead of claim 28, wherein the helix wire distal end extends around an eccentric path.

33. The lead of claim 28, wherein the distal end of the helix angles outward and extends approximately tangent to a circle defined by a proximal portion of the helix.

34. The lead of claim 28, wherein a proximal portion of the helix defines a circle, and wherein the distal end of the helix extends away from the circle in an eccentric path.

35. The lead of claim 28, wherein the fixation element helix extends over a portion of the distal insulation segment, and wherein the entire portion of the distal insulation segment over which the fixation element helix extends is offset from a centerline of the helix.

36. The lead of claim 28, wherein distal insulation segment is offset from a centerline of the fixation element helix such that each coil of the fixation element helix is offset from the distal insulation segment by distance that is greater on one side of the distal insulation segment than on an opposite side of the distal insulation segment.

37. The lead of claim 28, the fixation element helix extends over a portion of the distal insulation segment, and wherein the entire portion of the distal insulation segment over which the fixation element helix extends is straight.

* * * * *